United States Patent
Rothamel et al.

(10) Patent No.: US 10,214,461 B2
(45) Date of Patent: Feb. 26, 2019

(54) PROCESS AND PLANT FOR PRODUCING OLEFINS FROM OXYGENATES

(71) Applicant: L'Air Liquide, Societe Anonyme pour l'Etude et l'Exploitation des Procedes Georges Claude, Paris (FR)

(72) Inventors: Martin Rothamel, Frankfurt (DE); Stephane Haag, Frankfurt (DE); Frank Castillo-Welter, Frankfurt (DE); Peter Trabold, Frankfurt (DE); Martin Gorny, Frankfurt (DE); Sven Pohl, Frankfurt (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 14/843,139

(22) Filed: Sep. 2, 2015

(65) Prior Publication Data

US 2016/0068452 A1 Mar. 10, 2016

(30) Foreign Application Priority Data

Sep. 5, 2014 (DE) .................. 10 2014 112 792

(51) Int. Cl.
*C07C 1/20* (2006.01)
*C07C 41/01* (2006.01)
(Continued)

(52) U.S. Cl.
CPC .............. *C07C 1/20* (2013.01); *B01J 8/0453* (2013.01); *B01J 8/0492* (2013.01); *B01J 19/24* (2013.01);
(Continued)

(58) Field of Classification Search
CPC ........................................ C07C 1/20
See application file for complete search history.

(56) References Cited

U.S. PATENT DOCUMENTS 4,547,616 A * 10/1985 Avidan ................ C07C 1/20
585/639
5,817,906 A * 10/1998 Marker ................ C07C 1/20
203/28
(Continued)

FOREIGN PATENT DOCUMENTS

DE 197 23 363 12/1998
DE 10 027 159 12/2001
(Continued)

OTHER PUBLICATIONS

Geilen F.M.A.,et al, Butenes, Ullmann's Encyclopedia of Industrial Chemistry; 2013; pp. 1-13; Wiley-VCH Verlag GmbH & Co. KGaA, 2013, Weinheim, Germany.

*Primary Examiner* — In Suk C Bullock
*Assistant Examiner* — Alyssa L Cepluch
(74) *Attorney, Agent, or Firm* — Justin K. Murray

(57) ABSTRACT

A process for producing olefins from oxygenates can include the following steps: (i) heterogeneously catalyzed conversion of at least one oxygenate to a product stream containing $C_2$ olefins, $C_3$ olefins, $C_4$ olefins, $C_{5/6}$ hydrocarbon compounds, and $C_{7+}$ hydrocarbon compounds; and (ii) separation of a propylene stream consisting of $C_3$ olefins for at least 95 wt-%, wherein at least 10 wt-% of the propylene stream are recirculated into process step (i).

11 Claims, 1 Drawing Sheet

(51) Int. Cl.
*B01J 19/24* (2006.01)
*C07C 41/09* (2006.01)
*B01J 8/04* (2006.01)

(52) U.S. Cl.
CPC ............. *B01J 19/245* (2013.01); *C07C 41/01* (2013.01); *C07C 41/09* (2013.01); *B01J 2219/00006* (2013.01); *B01J 2219/24* (2013.01); *C07C 2521/04* (2013.01); *C07C 2529/40* (2013.01); *Y02P 30/42* (2015.11)

(56) References Cited

U.S. PATENT DOCUMENTS

| | | | |
|---|---|---|---|
| 8,269,056 B2 * | 9/2012 | Van Westrenen | C07C 1/20 585/638 |
| 8,444,940 B2 * | 5/2013 | Bach | B01J 4/002 422/618 |
| 2009/0124841 A1 * | 5/2009 | Rothaemel | B01D 3/143 585/639 |
| 2013/0165712 A1 * | 6/2013 | Sadasivan Vijayakumari | C07C 4/06 585/256 |

FOREIGN PATENT DOCUMENTS

| | | |
|---|---|---|
| DE | 10 2004 052 658 | 12/2005 |
| DE | 10 2005 048 931 | 4/2007 |
| DE | 10 2006 026 103 | 12/2007 |
| DE | 10 2009 031 636 | 1/2011 |
| EP | 0 448 000 | 9/1991 |

* cited by examiner

PROCESS AND PLANT FOR PRODUCING OLEFINS FROM OXYGENATES

CROSS REFERENCE TO RELATED APPLICATIONS

This application claims the benefit of priority under 35 U.S.C. § 119 (a) and (b) to German patent application No. DE102014112792.7, filed Sep. 5, 2014, the entire contents of which are incorporated herein by reference.

TECHNICAL FIELD OF THE INVENTION

The present invention relates to a process for producing olefins from oxygenates, which comprises the following steps: (i) heterogeneously catalyzed conversion of at least one oxygenate to a product stream containing $C_2$ olefins, $C_3$ olefins, $C_4$ olefins, $C_{5/6}$ hydrocarbon compounds and $C_{7+}$ hydrocarbon compounds, and (ii) separation of a $C_3$ stream consisting of propylene for at least 95 wt-%. Furthermore, the invention also comprises a plant for carrying out this process.

BACKGROUND OF THE INVENTION

Butenes, also called butylenes, are a group of four isomeric hydrocarbons with the common empirical formula $C_4H_8$, which have a C—C double bond and thus belong to the alkenes. Due to the C—C double bond, they are important starting substances for chemical syntheses and are required e.g. for the production of butanol, butanone, 1,3-butadiene or also plastics such as butyl rubber. Butene also is educt in the synthesis of methyl-tert-butyl ether (MTBE), which is one of the most important industrially used ethers.

Up to now, most of the $C_4$ olefins are produced by cracking of petroleum, in which long-chain hydrocarbons are split into short-chain hydrocarbons. During cracking, propylene, ethylene and aromatic hydrocarbons also are obtained beside $C_4$ olefins. In the cracking process, the yield of $C_4$ olefins however cannot be increased independent of other products. In addition, $C_2$ or $C_3$ olefins generally are preferred in cracking processes due to their higher market price. However, when the ethylene yield is maximized for example by changing the process conditions in typical cracking processes, the $C_4$ olefin yield decreases accordingly.

To satisfy the worldwide demand of butene, it therefore is necessary to resort to further production processes. Such a production process is the so-called MTP process, in which olefins are produced from methanol (MeOH) by catalytic conversion on a zeolitic catalyst. As is already suggested by the name methanol-to-propylene (MTP) process, the focus of this production process is on the recovery of propylene, but by shifting the process condition, the selectivity of the products obtained can be influenced and the product spectrum thus very well can also be shifted towards butenes.

The fundamentals of an MTP process are described for example in DE 10 2005 048 931 A1, in which olefins are produced from an educt mixture containing steam and oxygenates such as methanol and/or dimethyl ether. By a heterogeneously catalyzed reaction in at least one reactor, the educt mixture is converted to a reaction mixture comprising low-molecular olefins and gasoline hydrocarbons. By a suitable separation concept, higher olefins, above all the $C_{5+}$ fraction, can at least partly be recirculated into the reactor as recycling stream or for the most part be converted to propylene, whereby the yield of propylene is increased.

The MTP process usually has a propylene yield of about 65% (mole C). Previous MTP processes have in common that by an increased yield of propylene the economy of the process should be improved. DE 10 027 159 A1 for example describes an MTP process with two shaft reactors. For this purpose, methanol vapor is converted to dimethyl ether in a first, heterogeneously catalyzed process step. This dimethyl ether subsequently is split up into two partial streams and supplied to a first and a second shaft reactor, in which a product mixture containing propylene is produced on a zeolitic catalyst. The product stream of the first shaft reactor also is introduced into the second shaft reactor. A comparatively high amount of propylene of up to 50 vol-% thereby is achieved. At the same time, the process is very favorable in economic terms, since the expensive tubular reactors are replaced by comparatively inexpensive shaft reactors.

DE 10 2006 026 103 A1 describes another type of reactor for carrying out an MTP process. Gaseous oxygenates together with steam are converted to olefins at 400 to 470° C. in a closed reactor including several trays. The individual trays are filled with a fixed catalyst bed. Each tray individually is equipped with water and dimethyl ether and/or a liquid phase containing methanol, which is sprayed through several nozzle tubes. Thus, the optimum operating conditions can be set in each tray for a stream with this degree of conversion.

DE 10 2009 031 636 finally describes a process for producing the required oxygenates, in particular methanol and dimethyl ether, which is designed such that it is possible to flexibly switch between a methanol purification and a dimethyl ether production.

All previously known MTP processes have in common that they are optimized with regard to the yield of propylene. $C_4$ olefins, on the other hand, only are obtained as by-product and so far have not been in the focus of the procedure.

SUMMARY OF THE INVENTION

Therefore, it is the object of the present invention to provide a process and a plant for producing $C_4$ olefins.

According to the invention, this object is solved by a process with the features of certain embodiments disclosed herein.

A process for producing olefins from oxygenates in principle comprises the following steps:
(i) the heterogeneously catalyzed conversion of at least one oxygenate to a product stream containing $C_2$ olefins, $C_3$ olefins, $C_4$ olefins, $C_2$-$C_4$ paraffins, $C_{5/6}$ hydrocarbon compounds, and $C_{5+}$ hydrocarbon compounds, and
(ii) the separation of a $C_3$ stream consisting of propylene for at least 95 wt-%.

By recirculating this $C_3$ stream into the heterogeneously catalyzed conversion for at least 10 wt-%, preferably for at least 25 wt-%, particularly preferably for at least 50 wt-%, according to the invention, the yield of $C_4$ olefins can be increased.

While the propylene previously has been withdrawn completely and all recirculations into the heterogeneously catalyzed conversion were designed to the effect that the propylene yield is maximized, a decrease of the propylene yield now is accepted deliberately. Surprisingly, this recirculation actually leads to a higher rate of higher olefins, in particular of $C_4$ olefins, which only can be explained by chain-lengthening reactions. So far, only $C_{4+}$ fractions were recirculated into the reactor, in order to shorten their chain length by again passing the heterogeneously catalyzed conversion in a kind of cracking process.

The yield of $C_4$ olefins can be increased in particular in the case of a complete, i.e. 100 wt-%, recirculation of the propylene stream into the heterogeneously catalyzed conversion. It here is approvingly accepted that no propylene can be withdrawn from the plant as valuable product. Nevertheless, the process still is economic due to the increased yield of $C_4$ olefins.

However, a partial or complete recirculation of the $C_3$ stream and a lower or missing recirculation of the $C_4$ stream has the disadvantage that the exothermicity increases in the reactor, as under the reaction conditions the conversion of propylene is exothermal, whereas the conversion of butene proceeds endothermally. In addition, the paraffins (butanes) contained in the $C_4$ stream act as heat sink and help to limit the rise in temperature in the reactor.

For optimum reaction conditions, however, a narrow temperature window is obtained, as at too low temperatures less olefins are formed and at too high temperatures the catalyst would deactivate too fast. For this reason, the rise in temperature in the MTP reactor also should be minimized for a maximum olefin yield.

Correspondingly, under the new reaction conditions it must also be ensured that the adiabatic temperature increase in the reactor remains small.

It was found to be favorable to at least also recirculate a part of the $C_{5/6}$ hydrocarbon compounds and/or of the $C_7$ hydrocarbon compounds (which so far were part of the MTP gasoline product) into the heterogeneously catalyzed conversion, since the same are converted there into compounds with shorter carbon chains, preferably compounds with two to four carbon atoms. Since these reactions are strongly endothermal, this additional recirculation leads to an advantageous decrease of the adiabatic temperature increase.

By suitable conditions in the separation of the $C_7$ hydrocarbons from the remaining high-molecular fraction of the product mixture, the amount of helpful $C_7$ olefins and cyclic saturated hydrocarbons (also called $C_7$ naphthenes) can be maximized in this new recycle.

At the same time, the amount of toluene (a $C_7$ aromatic) can be minimized, which upon recirculation into the MTP process would lead to faster coking and hence to a reduction of the catalyst activity and due to undesired reactions with methanol (toluene+methanol→xylenes) would lead to a consumption of methanol which would reduce the possible olefin yield of the plant.

It was found to be particularly favorable when these hydrocarbon compounds with chains of five, six and/or seven carbon atoms contain an amount of ≤5 wt-%, preferably ≤2 wt-%, particularly preferably ≤1 wt-% of aromatic compounds.

The separation of the $C_7$ olefins and naphthenes from toluene and higher-molecular hydrocarbons here can be effected by separation processes known to the skilled person, wherein rectification columns were found to be particularly suitable. The use of a rectification column has the particular advantage that the MTP process according to the prior art at this point in the process scheme of processing already has such column, whose task it has been to at least partly separate $C_{6-}$ hydrocarbons at the top from $C_{6+}$ hydrocarbons at the bottom. This existing column can be converted to the new separation task with comparatively little effort, which in existing plants saves costs and time.

Furthermore, the adiabatic temperature increase in the reactor can further be reduced by selectively recirculating components as heat sink. According to the invention, a partial recirculation of the $C_4$ stream is useful for this purpose. The butanes contained therein are inert under the reaction conditions, but due to their thermal capacity would advantageously reduce the temperature increase in the reactor.

A separation of the butanes from the $C_4$ stream is particularly advantageous, as thus no valuable product butene is recirculated. A larger amount of butanes is present in the $C_4$ stream and anyway would have to be separated from the same at a suitable point. The separation of butane and butenes can be effected by separation processes known to the skilled person, wherein a separation by membrane is particularly useful in the present case. On the one hand, the $C_4$ stream for the separation is obtained at an elevated pressure of 10 bar and more in the course of the separating section, so that the pressure difference between retentate and permeate side advantageous for the performance of the membrane is present already and would not have to be produced first by additional pumps or compressors. On the other hand, membranes usually are much easier to use, in order to achieve a rough separation between substances. Especially this rough separation between butanes and butenes does not represent a disadvantage for the case of application in the process according to the invention, since butene residues in the butane recycle for the most part are converted to olefins in the MTP reactor, i.e. do not get lost. Butane residues in the butene product would not be disturbing at this point, since the butenes still have to be processed in the further course of the separating section.

The amount of the recirculated $C_4$ stream should be ≤20 wt-%, preferably ≤15 wt-%, particularly preferably 1.4 to 10.8 wt-% based on the total stream $C_4$, and the amount of the recirculated butanes should lie between 10 and 90 wt-% based on the total amount of all butanes produced.

In summary, it can be noted that by combining the additional $C_7$ recycling stream and the butane recycling stream the process for producing propylene and butylene from methanol according to the invention can be conducted in an optimum range in terms of reaction.

Furthermore, the process according to the invention permits a greater flexibility of the quantities produced by varying the recycling streams of propylene, butenes/butanes or butanes as well as $C_{5/6}$ and/or $C_{7+}$ hydrocarbon compounds. By suitable adaptation, the plant might produce both 100 wt-% of butenes/0 wt-% of propylene and 0 wt-% of butenes and 100 wt-% of propylene as well as any quantity ratio inbetween. The indications in percent each only relate to the sum of $C_3$ and $C_4$ olefins and do not account for the other by-products such as gasoline hydrocarbons or light gases such as methane, $H_2$, CO or propane.

In particular, there is a conversion of the desired product spectrum with its maximum in the region of the $C_4$ olefins, when the ratio of the molar sum of all recirculated olefins to the molar sum of the oxygenates used lies between 0.1 and 3. This means that between 0.1 and 3 mol of olefins per mol of oxygenates must be recirculated. What is preferred is a recirculation ratio of 0.75 to 1.6 mol of olefins per mol of oxygenates. Beside an increase in yield, the service life of the catalyst also can be prolonged. It is particularly preferred when the amount of recirculated hydrocarbons to the amount of supplied oxygenate also is adapted to the service life of the catalyst, wherein for older and hence less reactive catalysts a higher amount of oxygenate must be supplied, whereby a good yield of olefins also can be obtained with such less reactive catalysts.

In a preferred embodiment of the invention, the heterogeneously catalyzed conversion is split in two stages. In the first stage methanol is converted into dimethyl ether and in the second stage dimethyl ether is converted to a product stream containing $C_2$ olefins, $C_3$ olefins, $C_4$ olefins, $C_{5/6}$ olefins and $C_{7+}$ hydrocarbon compounds. This two-stage conversion provides for a better control of the reaction with regard to the temperature profile, since the exothermal conversion of methanol into DME can be decoupled from the main reaction and hence in turn a small adiabatic temperature increase in the MTP reactor can be realized, which is favorable for the olefin maximization.

In the sense of the invention, any further heterogeneously catalyzed conversion carried out in two stages also is possible, in which then in the first stage an alcohol is converted to the corresponding ether and subsequently in the second stage the ether is converted to the corresponding product stream.

It also was found to be favorable to separate water and non-converted methanol from the product stream after passing the heterogeneously catalyzed conversion, preferably after passing the second stage. Hence, the streams and thus the required plant volume are reduced. Moreover, water-free streams with lower energy demand can be separated into various fractions.

The separation of the water can be accomplished for example in a quench system, in that the product mixture is brought in contact with water and the aqueous phase is withdrawn from the quench. A fraction of the methanol-containing aqueous solution is evaporated and recirculated into the reactor. The other fraction of the methanol-containing aqueous solution is supplied to a methanol recovery.

Preferably, the separated methanol is guided back into the first stage for the conversion to dimethyl ether, while the steam is fed into the second stage of the heterogeneously catalyzed conversion and here can serve for moderating the reaction of the temperature problem. By this recirculation of methanol educt costs can be lowered, whereas the steam serves as inexpensive control variable for the temperature in the second stage of the heterogeneously catalyzed conversion.

In a two-stage heterogeneously catalyzed conversion, the second stage according to the invention is carried out at a temperature of 390 to 550° C., preferably at a temperature of 420 to 520° C.

The pressure in the reactor of the second stage preferably is higher than in the normal MTP process, since for maximizing the butene formation higher pressures are advantageous. At too high pressures, however, a conversion of methanol primarily is effected towards liquid hydrocarbons, so that in terms of reaction an optimum is obtained, which is about 2-3 bar at the reactor inlet and 1-2 bar at the reactor outlet.

Beside the changed product spectrum, the use of higher pressures has the advantage that the streams compressed more strongly require a small volume of the other technical configuration and the process control is simplified, since higher pressure losses are possible.

In a two-stage configuration, in which in the second stage dimethyl ether is converted to the product stream, it also was found to be favorable to introduce the dimethyl ether into the second stage partly in liquid form and partly in gaseous form. Due to the ratio of the liquid to the gaseous fraction of the dimethyl ether, the temperature profile within the second stage can be controlled, since with an increased liquid addition energy additionally is withdrawn from the system due to the evaporation enthalpy and thus cooling of the exothermal process occurs.

The invention furthermore comprises a plant with which olefins can be produced from oxygenates and which preferably is suitable for carrying out the process according to the invention. This plant includes the features of claim 11.

Such plant according to the invention comprises at least one reactor for the heterogeneously catalyzed conversion of at least one oxygenate to a product stream containing $C_2$ olefins, $C_3$ olefins, $C_4$ olefins, $C_{5/6}$ hydrocarbon compounds and $C_{7+}$ hydrocarbon compounds, and a separating device for separating a $C_3$ stream consisting of propylene for at least 95 wt-%. To maximize the yield of $C_4$ olefins and thus solve the object underlying the invention, the plant in addition includes a return conduit through which at least 10 wt-% of the propylene stream are recirculated into the heterogeneously catalyzed conversion.

Preferably, such plant includes a control device with which the amount of the recirculated propylene and of the discharged propylene can be determined flexibly.

Furthermore, it was found to be favorable when the plant includes at least one first reactor for a first conversion stage, in which methanol can at least partly be converted into dimethyl ether, and at least one second reactor for a second conversion stage, in which the stream containing dimethyl ether is converted to a product stream containing $C_2$ olefins, $C_3$ olefins, $C_4$ olefins, $C_{5/6}$ and $C_{7+}$ hydrocarbon compounds.

What also is preferred is a plant design in which the second reactor is designed with at least two fixed catalyst beds, preferably 2 to 6 fixed catalyst beds. In these fixed catalyst beds the catalyst is in a solid state, wherein the catalyst generally is a form-selective zeolite catalyst.

What is favorable here above all is a catalyst of the pentasil type with an alkali content of less than 400 ppm, preferably less than 200 ppm. The catalyst has a BET surface area of 300 to 600 $m^2/g$ and a pore volume (determined according to the mercury porosimetry) of 0.3 to 0.8 $m^3$. Analogously, there can also be used an $Al_2O_3$ catalyst, details of which can be found for example in EP 0 448 000 B1 and DE 197 23 363 A1.

Another preferred design of the plant according to the invention provides at least one further reactor for the second conversion stage, which is identical in construction with the used reactor of the second stage. Interruptions in the production of olefins as a result of maintenance work thereby can be avoided, in that the stream containing dimethyl ether each is introduced into one reactor and further converted there, while the second reactor is serviced and in particular the catalyst is regenerated.

The number of the reactors connected in parallel of course is not limited to two. In particular, it is preferred to use three reactors, two of which are equipped for the conversion of the oxygenate stream and one is equipped for regeneration.

The so-called regeneration of the catalyst preferably is effected with a hot, oxidant-containing gas having a temperature of 400 to 500° C., preferably 450 to 480° C., which instead of the educts is passed through the fixed catalyst beds. By this oxidant-containing gas, which preferably is a nitrogen-oxygen mixture, particularly preferably a nitrogen-air mixture, quite particularly air, carbonaceous deposits on the catalyst can be removed and the catalyst thus can be returned into its original state.

$C_x$ in the sense of the present application refers to all hydrocarbon compounds which have a carbon chain with exactly x carbon atoms, wherein x is a natural number. $C_{x-}$ designates hydrocarbon compounds which have x or less carbon atoms. $C_{x+}$ designates hydrocarbon compounds which contain x or more carbon atoms. $C_{x/y}$ designates compounds whose carbon chain includes x or y carbon atoms, wherein x and y are natural numbers.

All compounds with at least one double bond, in particular also those with more than one double bond (i.e. dienes, trienes, etc.) are referred to as olefins.

BRIEF DESCRIPTION OF THE DRAWINGS

Further features, advantages and possible applications of the invention can be taken from the following description of the drawing and the exemplary embodiments. All features described and/or illustrated form the subject-matter of the invention per se or in any combination, independent of their inclusion in the claims or their back-reference.

In the only FIGURE:

Figure 1:
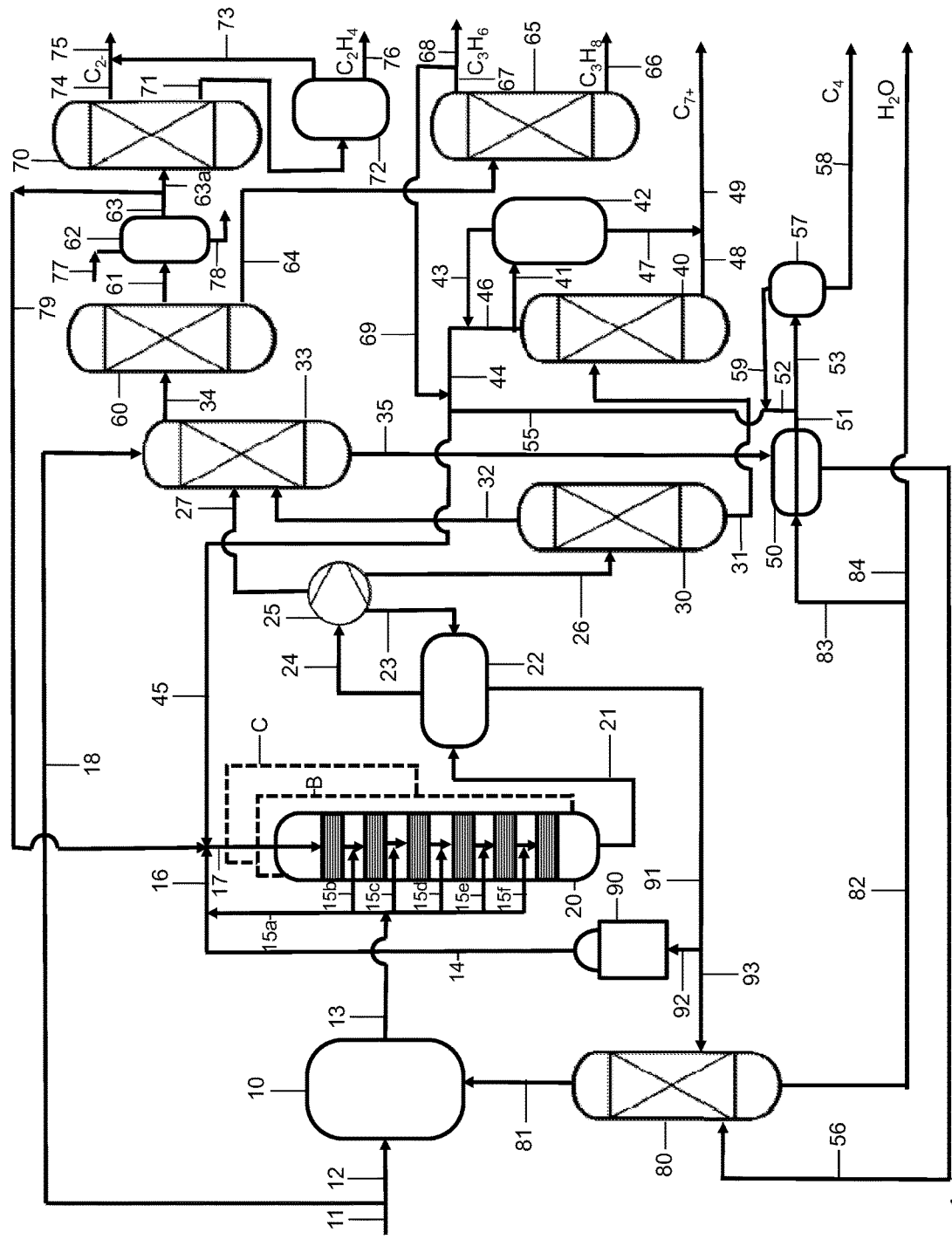

The FIGURE shows a plant according to the invention with partial recirculation of propylene.

DETAILED DESCRIPTION

The FIGURE shows the flow diagram of a plant or a process for the maximum yield of $C_4$ olefins proceeding from the educt methanol. The educt methanol can be fed in either in purified form (preferably with the US Federal Specification O-M-232 as grade AA) or as crude methanol. When crude methanol is used, a methanol purification is provided upstream of the illustrated plant, as is described e.g. in DE 10 2009 031 636.

Via conduits 11 and 12, the methanol is supplied to a reactor 10 for the production of dimethyl ether. Preferably, the methanol is evaporated and fed into the reactor 10 with a temperature of 230 to 280° C.

The dimethyl ether reactor 10 can be equipped as single-stage adiabatic fixed-bed reactor, wherein preferably an alumina catalyst is used for the conversion of the methanol to dimethyl ether. In the same way, however, other catalysts, preferably zeolites, can also be used.

Via conduits 13 and 14, the dimethyl ether obtained together with the water obtained in the reaction as well as non-converted methanol is supplied to a distributor conduit via which this intermediate product can then be charged to each individual tray of a reactor 20 by means of the conduits 15a, 15b, 15c, 15d, 15e and 15f. Charging to the first, uppermost tray is effected such that steam from conduit 14 and recirculated olefins from conduit 45 additionally are admixed to the mixture guided through conduit 15a and the resulting mixture subsequently is introduced into the reactor 20 via conduit 17.

The reactor 20 preferably is designed as fixed-bed reactor, as described in DE 10 027 159 or in DE 10 2006 026 103. The terms shaft reactor and fixed-bed reactor here are used as synonyms.

The used reactor 20 can identically be designed in double or triple form, as is indicated by B and C. This offers the advantage that in one or more reactors connected in parallel the dimethyl ether can be converted to olefins, while in the other reactors the catalyst is regenerated. Shut-down periods of the plant hence are avoided.

The entire reaction of the conversion of the oxygenates to olefins in the reactor 20 is exothermal, which is why between the individual reactor trays, within the individual reactor trays and/or also in the reactor 20 a cooling system can be provided. In the ideal case, an optimum temperature profile is adjusted by the cooling system in each tray, so that at the inlet of each tray a temperature of 400-480° C., preferably 420-470° C., and at the outlet after completion of the exothermal reactions a temperature of 440-540° C., preferably 460-510° C. is achieved.

A preferred possibility for cooling is the at least partial condensation of the stream 14, wherein a gaseous stream which contains DME and a liquid stream which contains water and methanol are obtained. When a two-phase, i.e. gaseous and liquid stream, is charged to at least one of the reactor beds, the temperature within the individual reactor bed can be controlled by the ratio of the liquid to the gaseous phase, since a liquid introduction leads to an evaporation within the stage, whereby heat is withdrawn from the system due to the evaporation enthalpy, and the system thus is cooled.

In that as mentioned already via conduits 14, 16, 17 a mixture containing steam is introduced into the reactor 20 via the first reactor bed, the temperature profile can even further be controlled, since due to its thermal capacity the added steam acts as heat sink and reduces the rise in temperature. By a rather homogeneous temperature profile within the individual reactor beds undesired side reactions, in particular a coking damaging the catalyst, are prevented and the reactions are carried out in a temperature range which is optimal for the maximization of the olefin formation.

Via conduit 21 a product mixture (product stream) then is withdrawn from the reactor 20, which contains olefins, steam, non-converted methanol and dimethyl ether, but also small amounts of naphthenes, paraffins as well as aromatics and further by-products. This mixture is supplied to a quench 22. In the quench system, the product mixture is cooled by one or more water circuits and the contained water substantially is condensed out. Due to the water obtained in the reaction and recirculated with the stream 14, a methanol-containing excess of water is obtained in the quench circuit. The same is discharged via conduit 91. The organic phase is supplied to the compressor 25 via conduit 24.

As further by-product of the conversion of the oxygenate stream organic acids are obtained. It can therefore be expedient to admix a pH-neutralizing chemical to the quenching medium via a non-illustrated dosing device, so as to neutralize the acids and prevent a corrosion of the plant sections.

To avoid poisoning of the catalyst by traces of e.g. sodium contained in the water, it may also be expedient to provide a distillation or an ion exchanger for purifying the circulated water.

After the quench system 22 an organic fraction, which carries at least 95 wt-% of the olefins contained in the product stream, is supplied to the compressor 25 via conduit 24. Since the gas is heated by the compression, it also is expedient to connect a non-illustrated heat exchanger in the subsequent conduit 27 and to thus cool and at least partly condense the gas. In a preferred aspect, four series-connected compressor stages are used and behind each compressor stage the gas is cooled and partly condensed out. By separation behind each individual compressor stage, a liquid and a gaseous fraction can be obtained comparatively sharply separated.

The liquid fraction is separated into an aqueous phase and a hydrocarbon phase. The aqueous phase is recirculated into the quench system 22 via conduit 23.

To prevent an accumulation of deposits within the at least one compressor 25, it is provided in a preferred aspect of the invention to supply a washing oil to the at least one compressor 25. This can be done continuously or section by section. Preferably, light gasoline obtained in the process is used as washing oil, so as not to introduce any additional compounds into the system.

Should the separation of the oxygenates from the product stream turn out to be unexpectedly problematic, it also is possible to connect a non-illustrated extraction and/or a wash before or after the quench 22 and/or before or after the compressor 25.

By condensing out, a rough separation can be carried out already in dependence on the chain length of the olefins obtained. This separation however is not selective for hydrocarbon compounds with four carbon atoms, so that the same are found in both fractions. Via conduit 26, the condensed $C_{4+}$ fraction is discharged. Via conduit 27, the $C_{4-}$ fraction, i.e. hydrocarbon compounds with 4 or less carbon atoms, is supplied to a separating device 33. In the separating device 33 the $C_{3-}$ hydrocarbons are separated from the $C_{4|}$ hydrocarbons, wherein the separation is carried out such that at least 95 wt-% of the $C_3$ hydrocarbons (i.e. propylene and propane) contained in stream 27 are present in stream 34, and that at least 95 wt-% of the $C_4$ hydrocarbons (butenes and butanes) contained in stream 27 are present in stream 35.

While the $C_{4+}$ fraction is supplied to a mixer/settler 50 via conduit 35, the $C_{3-}$ fraction is supplied to a rectification column 60 via conduit 34.

It was found to be particularly favorable to design the separation column 33 as extractive distillation, wherein in a particularly preferred aspect of the process methanol is used as extracting agent, since the same already is present in the process. The extractive distillation preferably is carried out as described in DE 10 2004 052 658 B3. Preferably, the methanol used as educt is utilized and fed into the column 33 via conduit 18.

After the $C_{3-}$ fraction has reached column 60 via conduit 34, the $C_3$ fraction is separated there from the $C_{2-}$ fraction. The pressure in the separating device 60 must be adapted such that on the one hand a suitable cooling medium can be selected in the condenser associated to the separation column 60, and on the other hand that in the compressor upstream of the separation column 60 a compression of the streams is possible. These problems are connected with the extremely low boiling point of the $C_{2-}$ and $C_3$ streams, which extremely limits the selection of cooling media which preferably are liquid at the corresponding temperatures. One possibility for the solution of these problems consists in operating the separating devices 30, 33 and 60 at about 20 bar and in the condenser of the separating device 60 use a cooling medium whose boiling point lies distinctly below the boiling point of propylene (−48° C. at 1 bar(a), 49° C. at 20 bar(a)). A second possibility consists in operating the separating devices 33 and 60 at a pressure which allows to use the same coolant in both separating devices 33 and 60 and in the associated non-illustrated condensers. A third possibility consists in operating all series-connected separating devices 30, 33 and 60 at about 20 bar and in using a compressor only in the head stream of the separating device 60, in order to employ a propylene separating agent as cooling medium in the condenser of the separating device 60.

The $C_{2-}$ fraction preferably withdrawn at the top is guided into a $CO_2$ separator 62 via conduit 61. For removing the $CO_2$ one or more alkali or alkaline earth lyes can be used, which are brought in contact with the gas stream via conduit 77. The same react with the carbon dioxide passed through to obtain carbonates which remain in the aqueous phase and along with the spent lye are discharged via conduit 78. In general, there is used a final washing solution with demineralized water, in order to prevent the breakthrough of $CO_2$.

Via conduit 63, the $C_{2-}$ fraction purified in this way subsequently is supplied to a separation column 70 designed in particular as rectification column, in which a fraction substantially containing methane is withdrawn over head. The separating conditions in column 70 are chosen such that at least 95 wt-% of the ethylene contained in stream 63 are present in stream 71.

After the separation of $CO_2$ a partial stream, which likewise is enriched in ethene, is again recirculated to the reactor 20 via conduit 79. On the one hand, the yield in propylene/butene can be increased therewith. On the other hand, the production quantity of ethylene thereby can be regulated.

Via conduit 71, the bottom product is fed into a $C_2$ splitter 72, in which on the one hand the valuable product ethene is discharged via conduit 76 and on the other hand ethane is admixed to conduit 74 via conduit 73 and thus is discharged via conduit 75. This gas can be utilized at another point of the process or also be sold e.g. as energy carrier.

The ethylene-containing stream from conduit 73, 74 and/or 75 can wholly or in part be recirculated into the reactor 20 via a non-illustrated conduit. On the one hand, the yield in propylene/butene thus can be increased and on the other hand the production quantity of ethylene can be regulated.

Since the amount of ethene product in the MTP process mostly is low, one process variant does without the purification of ethene and exclusively produces a recycle stream depleted of $CO_2$ and enriched in ethene, which is supplied to the reactor 20. Water and $CO_2$ definitely must have been removed before the stream is supplied to the separation column 70, as otherwise ice, dry ice and/or $CO_2$ hydrates are formed, which will clog the plant.

Via conduit 64, the $C_3$ fraction is passed from the column 60 into the column 65 preferably designed as rectification column. From this column 60, propane is withdrawn via the bottom and conduit 66. The valuable product propene is withdrawn via the head of column 65 and via conduit 67.

Via a non-illustrated flow control, up to 90 wt-% of the propene are discharged via conduit 68 and can be supplied to the market as valuable product. Via conduit 69, the propene is guided into conduit 44 and via conduits 45, 17 thus gets into the heterogeneously catalyzed conversion in the reactor 20.

From column 30, a $C_{4+}$ fraction furthermore is withdrawn from the bottom via conduit 31 and then gets into the distillation column 40. In the bottom, a gasoline stream which consists of the $C_{7+}$ fraction on the one hand is withdrawn from the same via conduit 48. Over head, the $C_{6-}$ fraction is withdrawn, which substantially contains hydrocarbon compounds with 5 or 6 carbon atoms. The column 30 is operated such that at least 50 wt-%, preferably more than 90 wt-%, of the $C_5$ hydrocarbons contained in the stream 31 get into the stream 46; and at least 50 wt-%, preferably more than 75 wt-% of $C_6$ hydrocarbons contained in stream 31 get into the stream 46. Furthermore, less than 10 wt-%, preferably less than 5 wt-% of the $C_6$ and $C_7$ aromatics (benzene and toluene) contained in stream 31 should get into the stream 46.

In particular with an increased propylene recycle, a $C_{7+}$ fraction can be separated in the head of column 40. The stream 46 additionally contains at least 25 wt-%, preferably more than 50 wt-%, of the $C_7$ hydrocarbons contained in stream 31.

Via conduit 41, at least a partial quantity of the stream 46 then is supplied to a gasoline stabilizer 42. Here, a partial quantity of the comparatively light $C_5$-$C_7$ components selectively is separated from 41 and via conduit 47 admixed to the heavier product from conduit 48. If necessary, the steam pressure of the resulting mixture which via conduit 49 leaves the plant boundary as gasoline product, thus can be adjusted to a higher value which hence is required for certain specifications.

Via conduit 43, the fraction containing $C_5$ and $C_6$ hydrocarbons gets into conduit 44 and from there into conduit 45, where it is fed into the reactor 20 together with the propylene.

In the mixer/settler 50, the $C_4$ fraction from column 30 is intensively mixed with water (stream 83), wherein two phases are formed after a resting phase. An aqueous phase containing oxygenates such as methanol and DME is separated and via conduit 56 supplied to the methanol recovery.

The organic phase containing the $C_4$ fraction is discharged via conduit 51.

Optionally, a part of the $C_4$ fraction can be returned into the reactor 20 as recycle via conduits 52, 45 and 17 depending on the demand of the plant. This can be expedient in particular when a co-production of propylene and butenes is to be carried out in the plant. By selective variation of the splitting ratio of stream 67 (propylene) into stream 69 (recycle) and stream 68 (product) and of stream 51 ($C_4$ fraction) into stream 52 (recycle) and stream 53 (product) the product spectrum of the plant can be varied within a large range. Propylene is recirculated with at least 10 wt-% and a maximum of 100 wt-%. From the $C_4$ fraction not more than 90 wt-% are recirculated, and in the case of the minimum the recirculation is omitted completely (0 wt-%).

As mentioned, a smaller recirculation of the $C_4$ fraction leads to an unfavorable change of the temperature profile in the reactor 20. According to the invention, however, this disadvantage can be compensated by the additional recycle of the $C_{5/6}$ and/or the $C_{7+}$ fraction as well as by the targeted recycle of butanes.

Correspondingly, stream 53 which beside olefinic hydrocarbons also contains paraffinic $C_4$ hydrocarbons optionally can be supplied to a suitable separating device 57, where by means of methods known to the skilled person a rough separation between butanes and the other $C_4$ components is effected. A separation by membrane is particularly recommendable in the present case, since stream 53 is obtained at an elevated pressure of at least 10 bar, so that the pressure difference between retentate and permeate side, which is advantageous for the performance of the membrane, is present already and would not have to be produced first by additional pumps or compressors.

The particularity of the application in this case consists in that no sharp separation, e.g. by distillation or extraction, is necessary. The objective is that stream 59 has a higher concentration of butanes than stream 53, while stream 58 has a lower concentration of butanes. Especially this rough separation between butanes and butenes does not represent a disadvantage for the case of application in the process according to the invention, since butene residues in the butane recycle for the most part are converted to olefins in the MTP reactor, i.e. do not get lost. Butane residues in the butene product would not be disturbing at this point, since the butenes still have to be processed in the further course of the separating section.

The fraction rich in butane leaves the separating device 57 via the stream 59 and is recirculated into the reactor together with the stream 52 via conduit 55.

The fraction poor in butane leaves the separating device 57 via the stream 58. A further purification of the $C_4$ fraction, which contains 1-butene, iso-butene, cis-2-butene, trans-2-butene as well as traces of butadiene, is not shown, but usually is carried out. The separation into the individual isomers as well as the separation of the butadiene is known in the literature (e.g. Frank Gehlen et al.: "Butenes" in Ullmann's Encyclopedia of Industrial Chemistry, published online 31 Jan. 2014). Butadiene usually is removed by extraction, e.g. with NMP (N-methylpyrrolidone) as extracting agent. Iso-butene is characterized by its higher chemical reactivity and e.g. by etherification with methanol on a suitable catalyst can be converted to methyl tert-butyl ether (MTBE) by reactive distillation and be separated. A summary of a suitable separation scheme is shown in Frank Gehlen et al.: "Butenes" (loc. cit.) in Fig. 3.

The aqueous stream containing methanol and DME, which is withdrawn from the mixer/settler 50 via conduit 56 is fed into the methanol recovery column 80 via conduit 55. From this methanol recovery column a head stream rich in methanol on the one hand is withdrawn via conduit 81 and introduced into the reactor 10 for the conversion of methanol to dimethyl ether. A water stream which is strongly depleted of organic impurities such as DME or methanol is withdrawn from the bottom via conduit 82 and partly used again for the mixer/settler via conduit 83. The remaining rest of water is discharged via conduit 86.

In a non-illustrated manner, excess water also can be used as cooling water in at least one component such as a reactor 10, 20 or also in the non-illustrated condensers of the separating columns 30, 33, 40, 60, 65, 70 described later.

In addition, the methanol recovery column 80 is fed by the aqueous methanol fraction from the quench 22 via conduits 91, 93. From this aqueous methanol solution parts of this stream are supplied to a steam generation 90 via conduit 92, from which steam is withdrawn via conduit 14 and supplied to the reactor 20 via conduits 16 and 17.

The advantage of the invention will be described with reference to the following exemplary embodiments.

EXEMPLARY EMBODIMENTS

Table 1 shows the typical distribution of an MTP process with full $C_4$ recycle, which is optimized for the propylene yield.

TABLE 1

Distribution of the $C_4$ compounds in the typical MTP process with $C_4$ recirculation

| | Yield in wt-% | Production in kt/a |
|---|---|---|
| Propylene | 28.4 | 470 |
| Propane | 0.8 | 13 |
| Gasoline fraction | 10.9 | 182 |
| $C_4$ (all) | 1.4 | 23 |
| Fuel (methane, ethane) | 0.7 | 11 |
| Ethylene | 1.4 | 23.2 |

Example 1

In Table 2, Example 1 shows the product spectrum of an MTP process in which 100 wt-% of the propylene are guided back into the olefin production.

TABLE 2

Product distribution in the MTP process with 100 wt-%
of C₃ recirculation (water is not indicated as product)

|  | Yield in wt-% | Production in kt/a |
|---|---|---|
| Propylene | 0 | 0 |
| Propane | 0 | 0 |
| Gasoline fraction | 12 | 201 |
| C₄ (all) | 26 | 442 |
| Fuel (methane, ethane) | 5.2 | 86 |

Example 2

In Table 3, Example 2 shows the product spectrum of an MTP process in which 50 wt-% of the propylene are guided back into the olefin production. One can see the direct correlation between propylene and $C_4$ yield.

TABLE 3

Product distribution in the MTP process with 50 wt-% of
C₃ recirculation. (Water is not indicated as product)

|  | Yield in wt-% | Production in kt/a |
|---|---|---|
| Propylene | 17.8 | 297 |
| Propane | 0.9 | 14 |
| Gasoline fraction | 9.3 | 156 |
| C₄ (all) | 12.9 | 241 |
| Fuel (methane, ethane) | 2.1 | 24 |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 10 reactor
11-19 conduit
20 reactor
21 conduit
22 quench
23, 24 conduit
25 compressor
26, 27 conduit
30 separating device
31, 32 conduit
33 separating device
34, 35 conduit
40 separating device
41 conduit
42 gasoline stabilizer
43-49 conduit
50 mixer/settler
51-56 conduit
57 separating device
58-59 conduit
60 separating device
61 conduit
62 CO₂ separator
63, 64 conduit
65 separating device
66-69 conduit
70 separating device
71 conduit
72 C₂ splitter
73-79 conduit
80 separating device
81-86 conduit
90 steam generation
91-93 conduit

We claim:

1. A process for producing olefins from oxygenates, the process comprising a first mode of operation for the production of propylene and a second mode of operation for the production of butylene,
   wherein the first mode of operation comprises the following steps:
   (i) heterogeneously catalyzed converting of at least one oxygenate to a product stream containing $C_2$ olefins, $C_3$ olefins, $C_4$ olefins, $C_{5/6}$ hydrocarbon compounds, and $C_{7+}$ hydrocarbon compounds, wherein the step of heterogeneously catalyzed converting is effected in two stages, wherein in the first stage methanol is converted with an equilibrium reaction into dimethyl ether and in the second stage dimethyl ether and unconverted methanol are converted to the product stream containing $C_2$ olefins, $C_3$ olefins, $C_4$ olefins, $C_{5/6}$ hydrocarbon compounds and $C_{7+}$ hydrocarbon compounds, wherein the second stage of the heterogeneously catalyzed conversion is operated at an operating temperature of 390° C. to 500° C.,
   (ii) recycling at least a portion of the $C_4$ olefins into the second stage;

(iii) separating a stream comprising the $C_3$ olefins from the product stream or a stream derived therefrom;

wherein the second mode of operation comprises the following steps:

(i) heterogeneously catalyzed converting of at least one oxygenate to a product stream containing $C_2$ olefins, $C_3$ olefins, $C_4$ olefins, $C_{5/6}$ hydrocarbon compounds, and $C_{7+}$ hydrocarbon compounds, wherein the step of heterogeneously catalyzed converting is effected in two stages, wherein in the first stage methanol is converted with an equilibrium reaction into dimethyl ether and in the second stage dimethyl ether and unconverted methanol are converted to the product stream containing $C_2$ olefins, $C_3$ olefins, $C_4$ olefins, $C_{5/6}$ hydrocarbon compounds and $C_{7+}$ hydrocarbon compounds, wherein the second stage of the heterogeneously catalyzed conversion is operated at an operating temperature of 390° C. to 500° C., (ii) recycling at least 10 wt-% of the $C_3$ olefins into the second stage;

(iii) separating a stream comprising the $C_4$ olefins from the product stream or a stream derived therefrom;

(iv) separating a stream comprising butane from the product stream or a stream derived therefrom;

(v) separating a stream comprising the $C_{5/6}$ hydrocarbon compounds from the product stream or a stream derived therefrom;

(vi) separating a stream comprising the $C_{7+}$ hydrocarbon compounds from the product stream or a stream derived therefrom;

(vii) recirculating of at least a portion of the $C_{5/6}$ hydrocarbon stream and the $C_{7+}$ hydrocarbon stream into the second stage in an amount effective to maintain the operating temperature of the second stage, wherein the second mode of operation has a higher amount of $C_3$ olefins recirculated to the second stage as compared to the first mode of operation, wherein the second mode of operation is configured to provide an increased yield in the $C_4$ olefins as compared to the first mode of operation.

2. The process as claimed in claim 1, wherein, during the second mode of operation, a ratio of a molar sum of all recirculated olefins to a molar sum of the oxygenates used lies between 0.75 and 3.

3. The process as claimed in claim 1, wherein if a determination is made that a service life of the catalyst is below a predetermined threshold, the amount of oxygenate used in step (ii) is increased in an amount to maintain olefin production.

4. The process as claimed in claim 1, wherein, during the second mode of operation an operating pressure of the second stage is increased as compared to the second stage of the first mode of operation.

5. The process as claimed in claim 4, wherein an inlet reactor pressure is 2-3 bar and an outlet reactor pressure is 1-2 bar.

6. The process as claimed in claim 1, wherein, during the second mode of operation, the dimethyl ether is introduced to the second stage in a combination of a liquid phase and a gaseous phase, wherein the ratio of the liquid phase to the gaseous phase is adjusted in order to control the temperature within the second stage.

7. The process according to claim 1, wherein during the second mode of operation, more than 90 wt-% of the $C_3$ olefins are recirculated into the second stage.

8. The process according to claim 1, wherein during the second mode of operation, an amount of aromatic compounds in the recirculated $C_{5/6}$ and/or $C_{7+}$ hydrocarbon streams is ≤5 wt-%.

9. The process according to claim 1, wherein up to 90 wt-% of the butane stream is recirculated into the second stage during the second mode of operation.

10. The process according to claim 1, wherein during the second mode of operation, the process further comprises the step of recirculating a portion of the butane stream into step (i) in an amount effective to maintain the operating temperature of the second stage.

11. The process according to claim 1, wherein during the first mode of operation, 100 wt-% of the $C_4$ olefins are recirculated into the second stage, and wherein the during the second mode of operation, 100 wt-% of the $C_3$ olefins and 0 wt-% of the $C_4$ olefins are recirculated into the second stage.

\* \* \* \* \*